US012458769B2

(12) United States Patent
Härmä et al.

(10) Patent No.: US 12,458,769 B2
(45) Date of Patent: Nov. 4, 2025

(54) CHINSTRAP ADJUSTMENT SYSTEM AND METHOD

(71) Applicant: KONINKLIJKE PHILIPS N.V., Eindhoven (NL)

(72) Inventors: Aki Sakari Härmä, Eindhoven (NL); Ulf Grossekathöfer, Eindhoven (NL); Rim Helaoui, Eindhoven (NL); Abhinay Maheshbhai Pandya, Eindhoven (NL); Sharon Baer, Pittsburgh, PA (US); William Weaver, III, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 363 days.

(21) Appl. No.: 18/073,850

(22) Filed: Dec. 2, 2022

(65) Prior Publication Data

US 2023/0173207 A1 Jun. 8, 2023

Related U.S. Application Data

(60) Provisional application No. 63/286,680, filed on Dec. 7, 2021.

(51) Int. Cl.

| | |
|---|---|
| ***A61F 5/56*** | (2006.01) |
| ***A61M 16/00*** | (2006.01) |
| ***A61M 16/06*** | (2006.01) |

(52) U.S. Cl.
CPC ............. *A61M 16/024* (2017.08); *A61F 5/56* (2013.01); *A61M 16/0694* (2014.02); *A61M 2205/3303* (2013.01)

(58) Field of Classification Search
CPC .. A61F 5/56; A61F 2005/563; A61F 5/05891; A61M 16/0694; A61M 16/0683;
(Continued)

(56) References Cited

U.S. PATENT DOCUMENTS

| | | | |
|---|---|---|---|
| 11,116,935 | B2 | 9/2021 | Grcia Molina |
| 11,497,883 | B2 | 11/2022 | Molina |

(Continued)

FOREIGN PATENT DOCUMENTS

| | | | |
|---|---|---|---|
| WO | WO2020232547 | A1 | 11/2020 |
| WO | WO2021152526 | A1 | 8/2021 |

OTHER PUBLICATIONS

Tsuda H. et al., “The Relationship Between Mouth Opening and Sleep Stage-Related Sleep Disordered Breathing”, Journal of Clinical Sleep Medicine (JCSM), vol. 7, issue 2, pp. 181-186, Apr. 15, 2011.

*Primary Examiner* — Ictoria Hicks Fisher
(74) *Attorney, Agent, or Firm* — Michael W. Haas

(57) ABSTRACT

An interface system for a user is provided that includes an interface unit configured to engage and selectively apply a force on a lower jaw of the user. An actuating unit is configured to actuate the interface unit in order to selectively apply and adjust the force on the lower jaw. One or more sensors are configured to generate output signals conveying information related to sleep stages of the user during a sleep session. The interface system further includes a processor configured to receive the output signals from the one or more sensors and determine a current sleep stage of the user. The processor controls the actuating unit based on the current sleep stage to adjust the force applied by the interface unit on the lower jaw.

17 Claims, 9 Drawing Sheets

(58) Field of Classification Search
CPC . A61M 16/0605; A61M 16/06; A61B 5/4812; A61B 5/682; A61B 5/4806; A61B 5/4818; A61B 5/6814; A61B 5/6803; A61B 5/08; A61B 5/0816; A61B 5/0826; A61B 5/4815; A61B 5/4542
See application file for complete search history.

(56) References Cited

U.S. PATENT DOCUMENTS

| | | | |
|---|---|---|---|
| 2004/0163648 | A1 | 8/2004 | Burton |
| 2016/0361512 | A1 | 12/2016 | Lawrenson |
| 2020/0306494 | A1 | 10/2020 | Molina |

CHINSTRAP ADJUSTMENT SYSTEM AND METHOD

CROSS-REFERENCE TO RELATED APPLICATIONS

This patent application claims the priority benefit under 35 U.S.C. § 119(e) of U.S. Provisional Application No. 62/286,680, filed on Dec. 7, 2021, the contents of which are herein incorporated by reference.

BACKGROUND OF THE INVENTION

1. Field of the Invention

The present invention relates generally to an interface system. More particularly, the present invention relates to an interface system, and a method for monitoring and controlling respiratory function of a user during a sleep session.

2. Description of the Related Art

During medical treatments, it may be sometimes desirable to deliver a flow of breathing gas non-invasively to an airway of a patient, i.e., without intubating the patient or surgically inserting a tracheal tube in their trachea. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA).

Non-invasive ventilation and pressure support therapies may involve the placement of a patient interface device in combination with a tubing assembly on a head of the patient. The patient interface device may comprise, without limitation, a nasal mask that covers the patient's nose, a nasal cushion having nasal prongs that are received within the patient's nares/nostrils, a nasal/oral mask that covers the nose and mouth, or a full-face mask that covers the patient's face. The patient interface device interfaces the ventilator or pressure support device with the airway of the patient, so that a flow of breathing gas can be delivered from a pressure/flow generating device to the airway of the patient.

During a sleep session, a person usually progresses through some stages of non-rapid eye movement (NREM) sleep and then enters REM sleep. Some patients suffering from OSA tend to open their mouths during the sleep session as they try to breathe in more amount of oxygen. Particularly, due to relaxing of muscles in deep sleep stages, a frequency of mouth opening is increased in deep sleep stages comprising one or more NREM sleep stages and REM stage. A positive air pressure in the mouth during the relaxing of the muscles may also provide an additional force for opening the mouth in the deep sleep stages. The opening of mouth may compromise an effectiveness of the CPAP therapy used by the patients suffering from OSA. For the sleep apnea patients, mouth opening during deep sleep may cause air provided by the CPAP therapy to leak out of the mouth, thereby leading to sore mouth and drying of sinuses, mouth, and throat. In some cases, a patient may wake up due to air leakage when the mouth is open in the sleep session.

The leakage due to relaxing muscles can be prevented by using a full-face mask that covers the nose and mouth of the patient. However, many people find a full-face mask unattractive because of the mask leaks, inconvenience of sleeping on side, and claustrophobic experience for a user. The main applications of the current invention are in mask types that do not cover the mouth of the user, for example, so called nasal masks or nasal pillow masks.

In nasal masks, the conventional ways to prevent the mouth from opening during deep sleep include use of a fixed chin strap to keep the mouth closed during the sleep session. Another conventional way is to use a medical tape to close the lips of the sleep apnea patient in order to prevent the mouth from opening. The conventional ways may be uncomfortable for the sleep apnea patient. Moreover, the conventional ways to prevent the mouth from opening may create a feeling of claustrophobia and a fear of suffocation for the sleep apnea patient if the airflow through the nose is interrupted or obstructed for some reason (e.g., functional faults in tubing assembly, nasal masks, compressor of the CPAP, etc.). Therefore, the conventional ways to prevent the mouth from opening in the sleep apnea patients during deep sleep may be uncomfortable and counterproductive.

SUMMARY OF THE INVENTION

Accordingly, a first aspect of the present invention relates to an interface system for a user. The interface system comprises an interface unit configured to engage and selectively apply a force on a lower jaw of the user. The interface system further comprises an actuating unit operatively coupled to the interface unit. The actuating unit is configured to actuate the interface unit in order to selectively apply and adjust the force on the lower jaw of the user. The interface system further comprises one or more sensors configured to generate output signals conveying information related to sleep stages of the user during a sleep session. The interface system further comprises a processor communicably coupled to the one or more sensors and the actuating unit. The processor is configured to receive the output signals from the one or more sensors and determine a current sleep stage of the user during the sleep session. The processor is further configured to control the actuating unit based on the current sleep stage of the user to adjust the force applied by the interface unit on the lower jaw of the user, thereby adjusting a degree of mouth opening of the user.

Accordingly, a second aspect of the present invention relates to a method for monitoring and controlling respiratory function of a user during a sleep session. The method comprises engaging a lower jaw of the user with an interface unit. The interface unit is configured to selectively apply a force on a lower jaw of the user. The method further comprises providing an actuating unit operatively coupled to the interface unit. The actuating unit is configured to actuate the interface unit in order to selectively apply and adjust the force on the lower jaw of the user. The method further comprises receiving, via the processor, output signals from one or more sensors conveying information related to sleep stages of the user during the sleep session. The method further comprises determining, via the processor, a current sleep stage of the user based on the output signals received from the one or more sensors. The method further comprises controlling, via the processor, the actuating unit based on the current sleep stage of the user to adjust the force applied by the interface unit on the lower jaw of the user, thereby adjusting a degree of mouth opening of the user.

A third aspect of the present invention relates to an interface system for monitoring and controlling respiratory function of a user. The interface system comprises interface means for engaging and selectively applying a force on a lower jaw of the user. The interface system further comprises actuating means for actuating the interface unit in order to selectively apply and adjust the force on the lower jaw of the user. The interface system further comprises sensor means for generating output signals conveying information related to sleep stages of the user during a sleep session. The interface system further comprises processing means for determining a current sleep stage of the user based on the output signals received from the sensor means. The processing means further controls the actuating means based on the current sleep stage of the user to adjust the force applied by the interface means on the lower jaw of the user, thereby adjusting a degree of mouth opening of the user.

A general object of the present invention is to provide an interface system for a user. The interface system is used during a sleep session to adjust a degree of mouth opening of the user during the sleep session based on a current sleep stage of the user. The degree of mouth opening of the user is controlled by selectively applying and adjusting a force applied by the interface system on a lower jaw of the user.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the scope of the appended claims.

BRIEF DESCRIPTION OF THE DRAWINGS

Exemplary embodiments disclosed herein may be more completely understood in consideration of the following detailed description in connection with the following figures. The figures are not necessarily drawn to scale. Like numbers used in the figures refer to like components. However, it will be understood that the use of a number to refer to a component in a given figure is not intended to limit the component in another figure labeled with the same number.

DETAILED DESCRIPTION OF EXEMPLARY EMBODIMENTS

Figure 1:
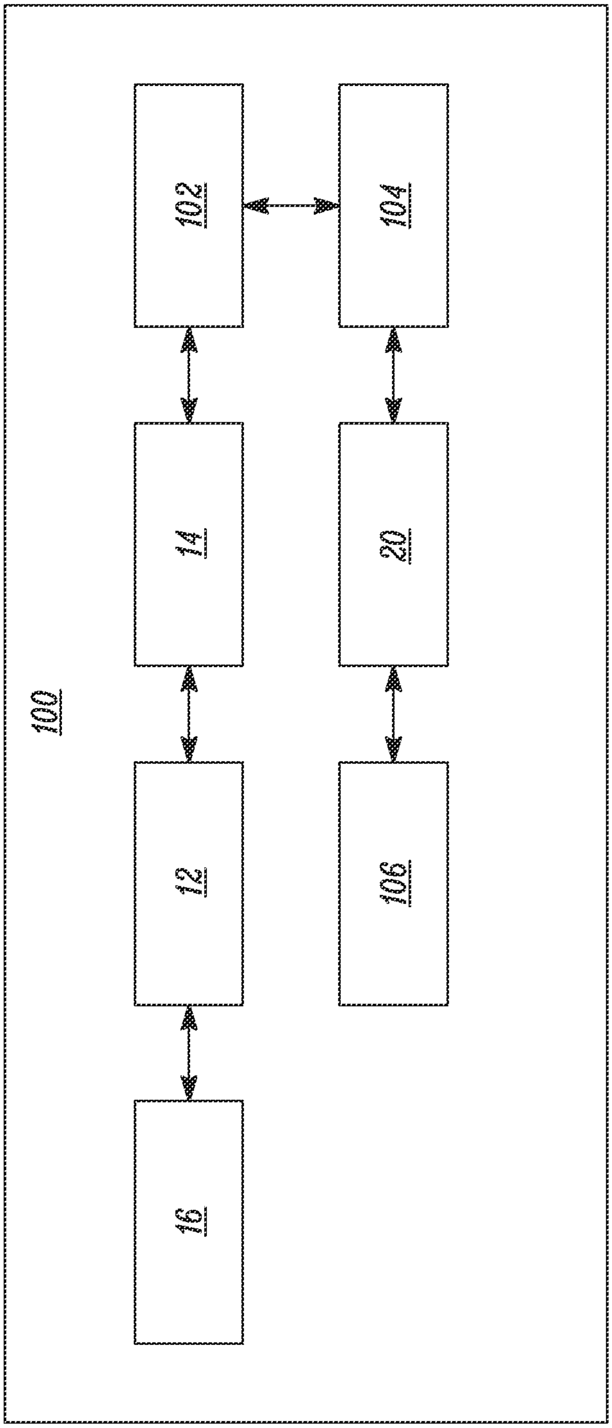
FIG. 1 is a block diagram of an interface system, according to an embodiment of the present invention.

In the following description, reference is made to the accompanying figures that form a part thereof and in which various embodiments are shown by way of illustration. It is to be understood that other embodiments are contemplated and may be made without departing from the scope or spirit of the appended claims. The following detailed description, therefore, is not to be taken in a limiting sense.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, the phrase "sealingly engage" shall mean elements which contact each other in a manner such that a generally air-tight seal is formed therebetween.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 2A:
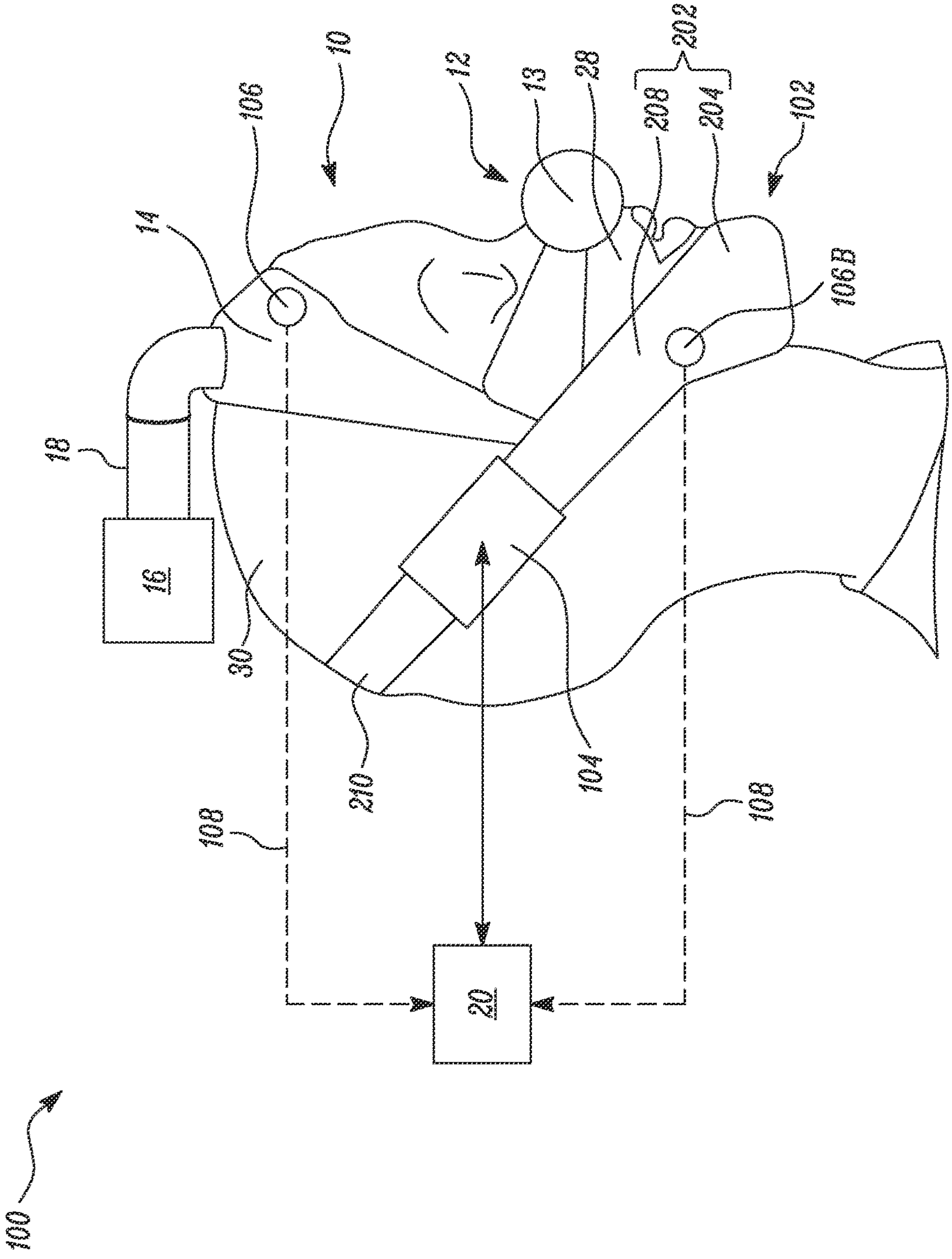
FIG. 2A is a side schematic view of the interface system of FIG. 1 for a user, according to a first embodiment of the present invention.
Figure 2C:
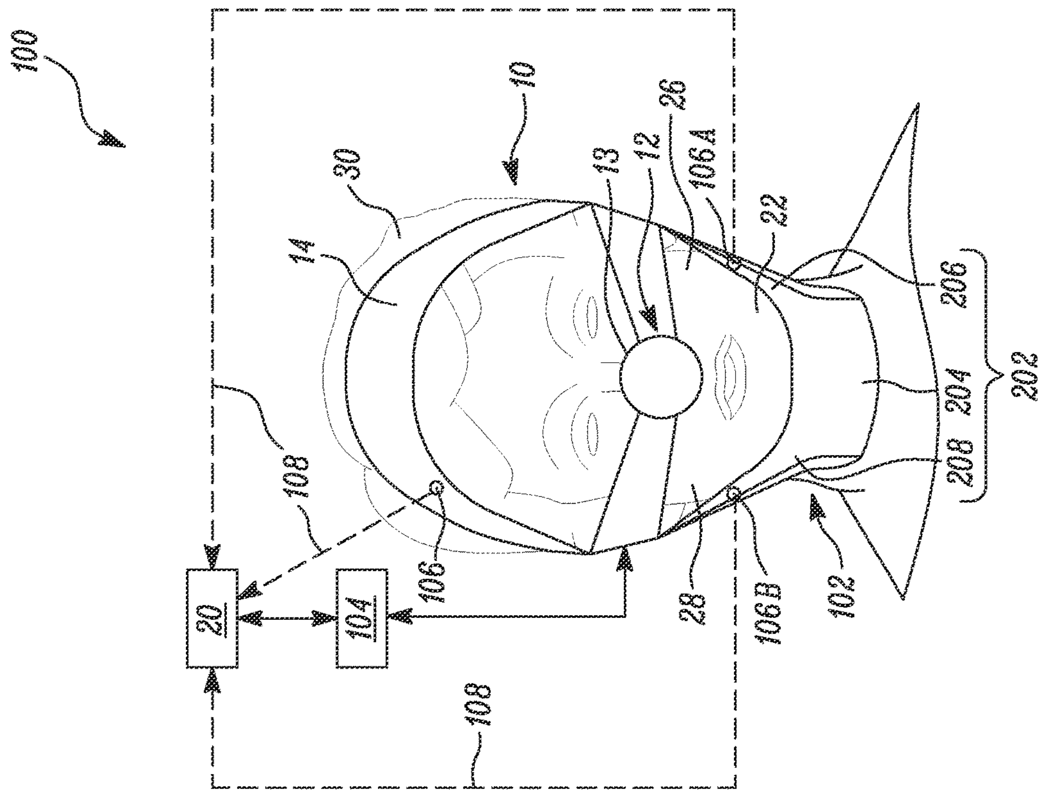
FIGS. 2B and 2C are front schematic views of the interface system of FIG. 2A in different tightness states, according to the first embodiment of the present invention.
Figure 2B:
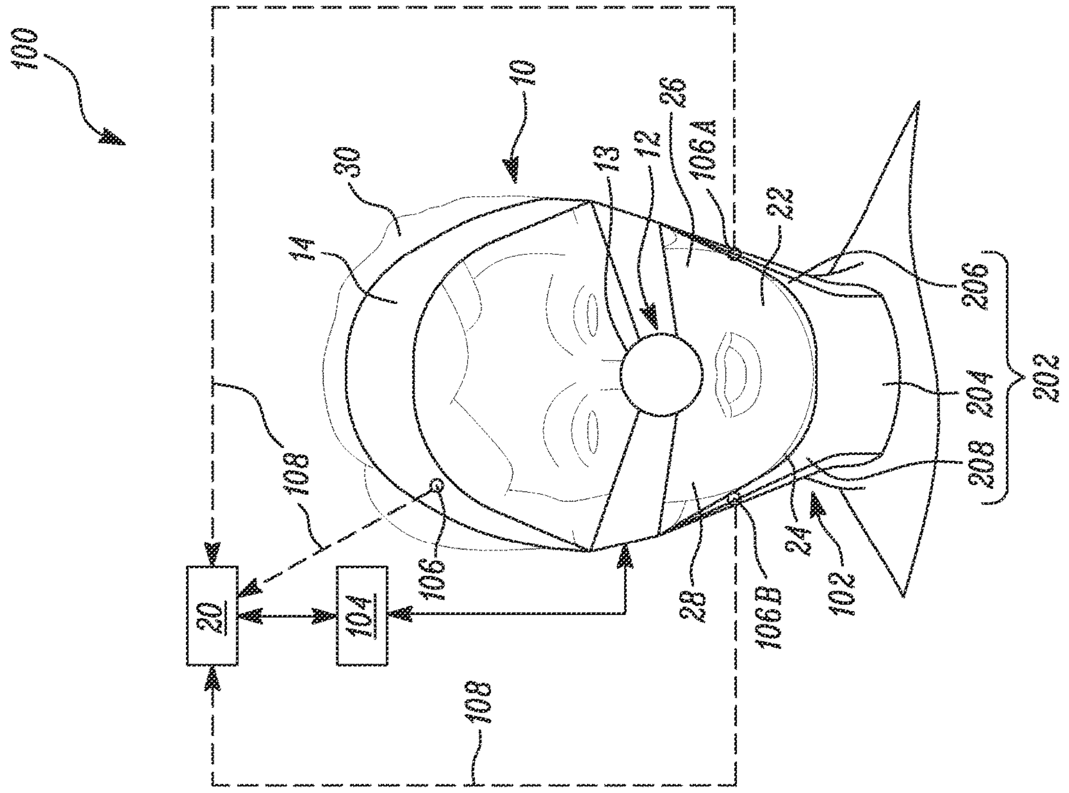

FIG. 1 illustrates a block diagram of an interface system 100 for a user 10 (shown in FIG. 2A), according to an embodiment of the present invention. Interface system 100 is configured to monitor and control respiratory function of user 10. FIGS. 2A to 2C illustrate different schematic views of interface system 100, according to a first embodiment of the present invention. Interface system 100 is used for monitoring and controlling respiratory function of user 10.

Referring to FIGS. 1 to 2C, interface system 100 comprises a respiratory interface device 12 structured to sealingly engage an airway of user 10. Interface system 100 further comprises a tubing assembly 14 disposed in fluid communication with respiratory interface device 12 to deliver a flow of breathing gas to the airway of user 10. Interface system 100 further comprises a pressure generating device 16 (shown schematically) structured to generate the flow of positive pressure breathing gas and deliver it to tubing assembly 14 via a conduit 18. Conduit 18 is structured to communicate the flow of breathing gas from pressure generating device 16 to respiratory interface device 12 through tubing assembly 14. Therefore, respiratory interface device 12 is configured to deliver the flow of breathing gas to the airway of user 10 received from pressure generating device 16 via conduit 18 and tubing assembly 14.

Pressure generating device 16 may comprise, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Conduit 18, tubing assembly 14, and respiratory interface device 12 are often collectively referred to as a user circuit.

Respiratory interface device 12 comprises a respiratory sealing element 13. In an exemplary embodiment, respiratory sealing element 13 may comprise a nasal cushion made of a soft, flexible material, such as, without limitation, silicone, an appropriately soft thermoplastic elastomer, a closed-cell foam, or any other suitable material or combination of such materials. It is to be appreciated, however, that any type of respiratory sealing element 13, such as a nasal/oral mask, a nasal pillow, or a full-face mask, which may facilitate a delivery of the flow of breathing gas to the airway of user 10, may be used in respiratory interface device 12. It should be noted that tubing assembly 14, in conjunction with additional attachments, may allow coupling of different types of respiratory interface devices, without any limitations.

Interface system 100 further comprises one or more sensors 106 configured to generate output signals 108 conveying information related to sleep stages of user 10 during a sleep session. In various exemplary embodiments, one or more sensors 106 may be interchangeably referred to as "sensor means 106". Therefore, interface system 100 comprises sensor means 106 for generating output signals 108 conveying information related to sleep stages of user 10 during the sleep session. Output signals 108 conveying information related to sleep stages of user 10 may include information related to brain activity in user 10, cardiac activity in user 10, and/or other physiological activity in user 10. As such, one or more sensors 106 are configured to generate output signals 108 conveying information related to brain activity, cardiac activity, and/or other activity in user 10. In various exemplary embodiments, one or more sensors 106 are configured to generate output signals 108 conveying information related to stimulation provided to user 10 during sleep sessions. In other embodiments, information conveyed by output signals 108 from one or more sensors 106 may be used to control a sensory stimulator to provide sensory stimulation to user 10.

In the illustrated embodiment of FIGS. 2A to 2C, one of one or more sensors 106 is disposed on tubing assembly 14. The location of one or more sensors 106 is not intended to be limiting. In other embodiments, one or more sensors 106 may be disposed in a plurality of locations, such as for example, within (or in communication with) a sensory stimulator (not shown), removably coupled with clothing of user 10, worn by user 10 (e.g., as a headband, a wristband, etc.), positioned to point at user 10 while user 10 is sleeping (e.g., a camera that conveys output signals 108 related to movement of user 10), coupled with a bed and/or other furniture where user 10 is sleeping, and/or in other locations.

In various exemplary embodiments, one or more sensors 106 comprise at least one of an electroencephalogram (EEG) sensor, an electrocardiogram (ECG) sensor, a photoplethysmography (PPG) sensor, an air flow sensor, a microphone, a humidity sensor, a carbon dioxide sensor, an accelerometer, a bioimpedance sensor, and an image sensor.

In various exemplary embodiments, one or more sensors 106 may generate output signals 108 that directly convey information related to brain activity of user 10. For example, one or more sensors 106 may include EEG electrodes configured to detect electrical activity along the scalp of user 10 resulting from current flows within the brain of user 10. In various exemplary embodiments, one or more sensors 106 may generate output signals 108 that indirectly convey information related to brain activity of user 10. For example, one or more sensors 106 may comprise a heart rate sensor that generates an output based on a heart rate of user 10 (e.g., a sensor 106 may be a heart rate sensor than can be located on the chest of user 10, and/or be configured as a bracelet on a wrist of user 10, and/or be located on another limb of user 10). In various exemplary embodiments, one or more sensors 106 may generate output signals 108 based on a movement of user 10, a respiration of user 10, and/or other characteristics of user 10.

In various exemplary embodiments, one or more sensors 106 comprising the accelerometer may be carried or disposed on a wearable device, such as a bracelet around the wrist and/or ankle of user 10, such that sleep may be analyzed using actigraphy signals. In various exemplary embodiments, one or more sensors 106 comprising the bioimpedance sensor enable measuring important physiological parameters required to determine the current sleep stage of user 10. For example, the bioimpedance sensor may be used to perform brain and pulmonary function monitoring, impedance cardiography, pneumography, and so on.

In various exemplary embodiments, one or more sensors 106 may comprise an electrooculogram (EOG) electrode, an actigraphy sensor, an ECG electrode, a respiration sensor, a pressure sensor, a vital signs camera, a functional near infra-red sensor (fNIR), a temperature sensor, and/or other sensors configured to generate output signals 108 related to (e.g., the quantity, frequency, intensity, and/or other characteristics) the stimulation provided to user 10, the brain activity of user 10, the cardiac activity of user 10, and/or any other physiological parameter of user 10.

In various exemplary embodiments, one or more sensors 106 may be grouped into one or more singular devices. For example, one or more sensors 106 may be included in a headset and/or other garments worn by user 10. Such a headset may include, for example, sensing electrodes, a reference electrode, and one or more devices associated with an EEG. The reference electrode may be located behind the ear of user 10 or in other locations. In this example, the sensing electrodes may be configured to generate output signals 108 conveying information related to brain activity of user 10, and sleep stages of user 10 during the sleep session.

In various exemplary embodiments, at least one of one or more sensors 106 is configured to detect a degree of mouth opening of user 10. For example, one or more sensors 106 comprising the accelerometer may detect changes in mouth opening of user 10 during the sleep session.

Interface system 100 further comprises a processor 20 communicably coupled to one or more sensors 106. Processor 20 may be a programmable analog and/or digital device that can store, retrieve, and process data. In an application, processor 20 may be a controller, a control circuit, a computer, a workstation, a microprocessor, a microcomputer, a central processing unit, a server, or any suitable device or apparatus. Processor 20 may comprise one or more of a digital processor, an analog processor, a digital circuit designed to process information, an analog circuit designed to process information, a state machine, and/or other mechanisms for electronically processing information. In other embodiments, processor 20 may comprise a plurality of processing units. These processing units may be physically located within interface system 100, or the processing units may be located remotely from interface system 100. In various exemplary embodiments, processor 20 may be interchangeably referred to as "processing means 20".

Processor 20 is configured to receive output signals 108 from one or more sensors 106 and determine a current sleep stage of user 10 during the sleep session. In other words, interface system 100 comprises processing means 20 for determining the current sleep stage of user 10 based on output signals 108 received from sensor means 106. Processor 20 may detect and/or predict the current sleep stage of user 10 based on various methods. For example, one of the methods to detect the current sleep stage of user 10 is provided in U.S. patent application Ser. No. 16/724,536, filed Dec. 23, 2019, entitled "System and method for enhancing rem sleep with sensory stimulation", the contents of which are incorporated herein by reference.

Initially, according to the method, a machine learning model is trained by using historical sleep stage information associated with one or more users. In various exemplary embodiments, the machine learning model is trained by providing the historical sleep stage information as an input to the machine learning model. In various exemplary embodiments, the machine learning model may be and/or include mathematical equations, algorithms, plots, charts, networks (e.g., neural networks), and/or other tools, and machine learning model components. For example, the machine learning model may be and/or include one or more neural networks having an input layer, an output layer, and one or more intermediate or hidden layers, and/or any other supervised machine learning algorithms. In various exemplary embodiments, the one or more neural networks and/or any other supervised machine learning algorithms may be and/or include deep neural networks (e.g., neural networks that have one or more intermediate or hidden layers between the input and output layers). Therefore, processor 20 may detect the current sleep stage of user 10 based on output signals 108 and the machine learning model comprising neural networks.

The current sleep stage detected by processor 20 may be associated with REM sleep, non-rapid eye movement (NREM) sleep, and/or other sleep. For example, the current sleep stage detected by processor 20 may be a first NREM sleep stage N1 (shown in FIG. 4), a second NREM sleep stage N2 (shown in FIG. 4), and/or a REM sleep stage R1 (shown in FIG. 4). In first NREM sleep stage N1, user 10 is in light sleep and respiration slows down. Further, in first NREM sleep stage N1, muscles relax, and heart rate also decreases. In second NREM sleep stage N2, user 10 is in deep sleep and user's body promotes muscle growth and repair. Further, in second NREM sleep stage N2, blood pressure drops and waking up is relatively difficult. In REM sleep stage R1, respiration as well as heart rate increases. Further, in REM sleep stage R1, temperature regulation is switched off and vivid dreams may occur.

With reference to FIGS. 1 to 2C, interface system 100 further comprises an interface unit 102 configured to engage and selectively apply a force F (shown in FIG. 4) on lower jaw 22 (also shown in FIG. 2B) of user 10. Specifically, interface unit 102 is configured to engage and selectively apply force F on at least one of the temporomandibular joints. Each of the two temporomandibular joints is a hinge that connects the jaw to temporal bones of the skull.

One may consider that force F is applied to lower jaw 22 and another, equivalent counterforce is applied to the skull to keep it immobilized. Similarly, one may consider that the same angular momentum on the hinge may be created by applying a force to the skull and a support to lower jaw 22. The effect on the temporomandibular joint in both cases is an angular momentum, which acts towards closing of the mouth. In a case of a strap, we have a full duality, and these two interpretations are equivalent. In the following description and the claims we state, for brevity, that the "force is applied to the lower jaw" but it should be clear based on elementary physics that equivalent dual interpretations of the directions of the acting forces is possible.

In various exemplary embodiments, force F may be applied to electrically stimulate the mandibular branch of the trigeminal nerve. The electrical stimulation of the mandibular branch may further cause the masseter muscle to contract which acts towards closing of the mouth.

In various exemplary embodiments, interface unit 102 may be interchangeably referred to as "interface means 102". Therefore, interface system 100 comprises interface means 102 for engaging and selectively applying force F on lower jaw 22 of user 10. In the illustrated embodiment of FIGS. 2A to 2C, interface unit 102 comprises a strap 202 configured to be at least partially worn on a chin 24 (shown in FIG. 2B) of user 10 and apply force F on lower jaw 22 of user 10 based on a tightness of strap 202. In various exemplary embodiments, tubing assembly 14 is coupled to interface unit 102. In an example, tubing assembly 14 may be coupled to interface unit 102 by using Velcro® hook-and-loop fasteners or a similar attachment means.

In FIG. 2C, strap 202 is shown to have a greater tightness than strap 202 shown in FIG. 2B. Due to decreased tightness of strap 202 in FIG. 2B, the degree of mouth opening of user 10 in FIG. 2B is higher than the degree of mouth opening of user 10 in FIG. 2C.

With reference to FIGS. 2A to 2C, in various exemplary embodiments, strap 202 comprises a chin portion 204, a first lateral portion 206, and a second lateral portion 208. Chin portion 204 is configured to be disposed on chin 24 of user 10. First lateral portion 206 is coupled to chin portion 204 and configured to be disposed on a first cheek 26 of user 10. Second lateral portion 208 is coupled to chin portion 204 opposite to first lateral portion 206 and configured to be disposed on a second cheek 28 of user 10. In various exemplary embodiments, each of first and second lateral portions 206, 208 may be coupled to chin portion 204 by using Velcro® hook and loop fasteners or the like. In some other embodiments, chin portion 204, first lateral portion 206, and second lateral portion 208 may be integral with each other.

In various exemplary embodiments, interface unit 102 further comprises a headband 210 (shown in FIG. 2A) configured to be worn on a head 30 of user 10 and coupled to first lateral portion 206 and second lateral portion 208 of strap 202. Headband 210 may be coupled to each of first and second lateral portions 206, 208 by using Velcro® hook and loop fasteners or the like.

In various exemplary embodiments, one or more sensors 106 comprise a set of first sensors 106A disposed on first lateral portion 206 of strap 202 and a set of second sensors 106B disposed on second lateral portion 208 of strap 202. In other embodiments, one or more sensors 106 may further comprise additional sets of sensors disposed on various locations on strap 202. In other embodiments, one or more sensors 106 may further comprise additional sets of sensors 106 disposed in other locations outside strap 202 or interface unit 102.

Interface system 100 further comprises an actuating unit 104 operatively coupled to interface unit 102. Specifically, actuating unit 104 is configured to actuate interface unit 102 in order to selectively apply and adjust force F on lower jaw 22 of user 10. In various exemplary embodiments, actuating unit 104 may be interchangeably referred to as "actuating means 104". Therefore, interface system 100 comprises actuating means 104 for actuating interface unit 102 in order to selectively apply and adjust force F on lower jaw 22 of user 10. Actuating unit 104 is schematically shown in FIGS. 2B and 2C for the purpose of illustration.

Processor 20 is communicably coupled to actuating unit 104. Processor 20 (or processing means 20) is further configured to control actuating unit 104 (or actuating means 104) based on the current sleep stage of user 10 to adjust force F applied by interface unit 102 on lower jaw 22 of user 10, thereby adjusting a degree of mouth opening of user 10. Therefore, processor 20 is configured to control actuating unit 104 based on the degree of mouth opening of user 10. In the illustrated embodiment of FIGS. 2A to 2C, actuating unit 104 is further configured to adjust the tightness of strap 202 on chin 24 of user 10 in order to control the degree of mouth opening. In various exemplary embodiments, processor 20 is further configured to control actuating unit 104 to adjust the tightness of strap 202 based on the current sleep stage. In general, the degree of mouth opening of user 10 tends to decrease with increased tightness of strap 202 and vice versa.

Figure 3:
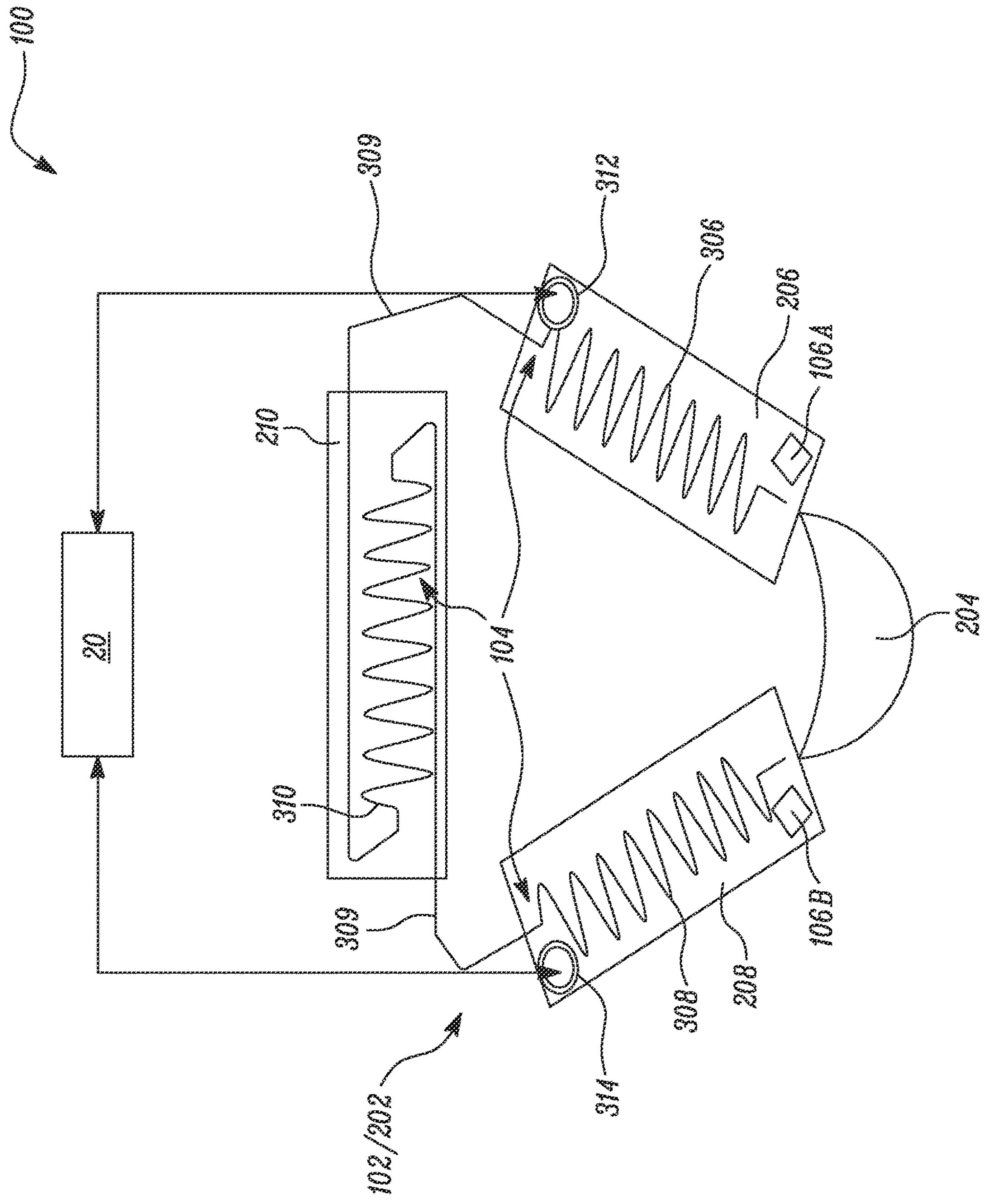
FIG. 3 is a schematic perspective view of the interface system of FIG. 2A illustrating a detailed representation of an actuating unit, according to the first embodiment of the present invention.

FIG. 3 is a schematic perspective view of interface system 100 illustrating actuating unit 104 and strap 202 in detail, according to an embodiment of the present invention. In the illustrated embodiment of FIG. 3, actuating unit 104 comprises a first lateral spring 306 coupled to first lateral portion 206 of strap 202. First lateral spring 306 may be disposed within first lateral portion 206 of strap 202. In various exemplary embodiments, set of first sensors 106A disposed on first lateral portion 206 is located proximal to first lateral spring 306. Actuating unit 104 further comprises a second lateral spring 308 coupled to second lateral portion 208 of strap 202. Second lateral spring 308 may be disposed within second lateral portion 208 of strap 202. In various exemplary embodiments, set of second sensors 106B disposed on second lateral portion 208 is located proximal to second lateral spring 308.

Actuating unit 104 further comprises a head spring 310 configured to be disposed on head 30 of user 10 and coupled to each of first lateral spring 306 and second lateral spring 308. Head spring 310 is coupled to headband 210. In various exemplary embodiments, each of head spring 310, first lateral spring 306, and second lateral spring 308 is directly or indirectly coupled to each other via a string 309. In various exemplary embodiments, each of head spring 310, first lateral spring 306, and second lateral spring 308 may be a coil spring.

Actuating unit 104 further comprises a first motor mechanism 312 operatively coupled to first lateral spring 306 and configured to extend or compress first lateral spring 306. Actuating unit 104 further comprises a second motor mechanism 314 operatively coupled to second lateral spring 308 and configured to extend or compress second lateral spring 308. Processor 20 is communicably coupled to each of first motor mechanism 312 and second motor mechanism 314.

Extension or compression of each of first lateral spring 306 and second lateral spring 308 causes a corresponding compression or extension of head spring 310. In the illustrated embodiment of FIG. 3, compression of each of first lateral spring 306 and second lateral spring 308 causes the corresponding extension of head spring 310. Similarly, extension of each of first lateral spring 306 and second lateral spring 308 causes the corresponding compression of head spring 310.

Further, first motor mechanism 312 and second motor mechanism 314 are configured to extend or compress first lateral spring 306 and second lateral spring 308, respectively, by adjusting a tension in string 309. For example, first motor mechanism 312 and second motor mechanism 314 are configured to compress first lateral spring 306 and second lateral spring 308, respectively, by pulling string 309. Compression of first lateral spring 306 and second lateral spring 308 results in extension of head spring 310.

In various exemplary embodiments, each of first motor mechanism 312 and second motor mechanism 314 may comprise at least a rotor, a stator surrounding the rotor, an output shaft, and a winding. Components of first motor mechanism 312 and second motor mechanism 314 are not shown in FIG. 3 for illustrative purposes. The rotor of first motor mechanism 312 is rotatable relative to the stator of first motor mechanism 312. The rotor of second motor mechanism 314 is rotatable relative to the stator of second motor mechanism 314. The output shaft of each of first motor mechanism 312 and second motor mechanism 314 may be coupled to string 309 to extend or compress first lateral spring 306. A rotation of the rotor of first motor mechanism 312 causes turning of the output shaft of first motor mechanism 312 which further adjusts the tension in string 309. A rotation of the rotor of second motor mechanism 314 causes turning of the output shaft of second motor mechanism 314 to adjust the tension in string 309. Moreover, extension or compression of each of first lateral spring 306 and second lateral spring 308 causes a corresponding increase or decrease of the tightness of strap 202.

In the illustrated embodiment of FIG. 3, compression of each of first lateral spring 306 and second lateral spring 308 causes the tightness of strap 202 to increase. Similarly, extension of each of first lateral spring 306 and second lateral spring 308 causes the tightness of strap 202 to decrease. Processor 20 is configured to control first motor mechanism 312 and second motor mechanism 314 in order to adjust the tightness of strap 202. Based on output signals 108 (shown in FIG. 2A) received from one or more sensors 106, processor 20 controls first motor mechanism 312 and second motor mechanism 314 of actuating unit 104 in order to adjust the tightness of strap 202. In other words, based on the current sleep stage of user 10, processor 20 controls first motor mechanism 312 and second motor mechanism 314 of actuating unit 104 in order to adjust the tightness of strap 202. Therefore, based on the current sleep stage of user 10, processor 20 controls first motor mechanism 312 and second motor mechanism 314 of actuating unit 104 in order to control the degree of mouth opening of user 10.

Figure 4:
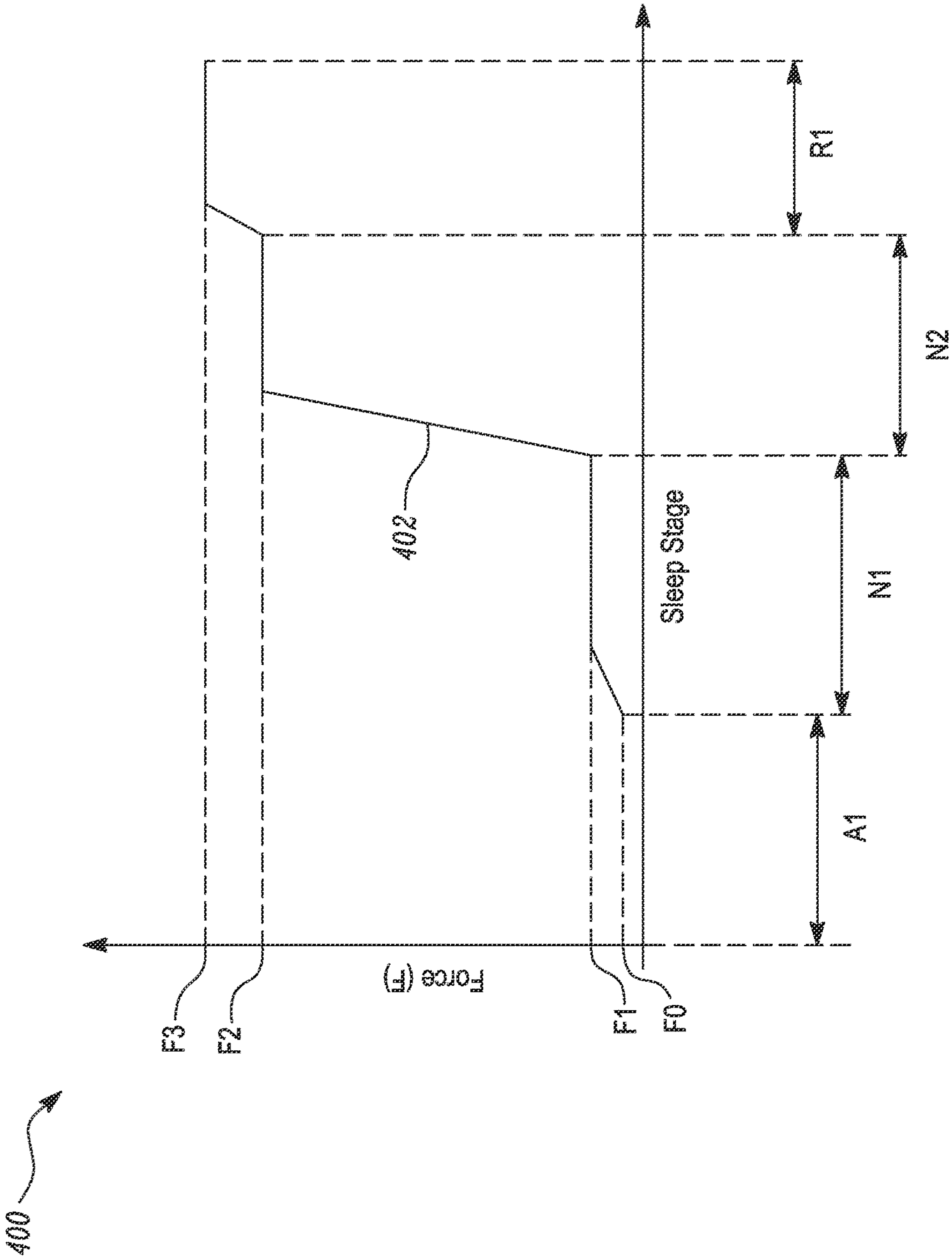
FIG. 4 is a graph illustrating a plot between force applied by an interface unit of the interface system of FIG. 1 and different sleep stages of the user, according to an embodiment of the present invention.

FIG. 4 is a graph 400 illustrating a plot 402 between force F applied by interface unit 102 and different sleep stages of user 10, according to an embodiment of the present invention. Force F applied by interface unit 102 is depicted in arbitrary units (a.u.) on the ordinate. Different sleep stages of user 10 are depicted on the abscissa.

Referring to FIGS. 1 to 4, in an awake state A1 of user 10, processor 20 is configured to control actuating unit 104 which further actuates interface unit 102, such that force F applied by interface unit 102 on lower jaw 22 is an idle force level F0. Specifically, with reference to FIGS. 2A to 4, in awake state A1 of user 10, force F applied by strap 202 on lower jaw 22 equals idle force level F0.

In various exemplary embodiments, processor 20 is further configured to increase force F applied by interface unit 102 in a stepwise manner to a first force level F1 from idle force level F0 corresponding to awake state A1 upon detection of first NREM sleep stage N1. In other words, once user 10 transitions from awake state A1 to first NREM sleep stage N1 during the sleep session, processor 20 receives output signals 108 conveying information related to first NREM sleep stage N1, and force F applied by interface unit 102 is increased from idle force level F0 to first force level F1. Specifically, upon detection of first NREM sleep stage N1, processor 20 controls actuating unit 104, such that force F applied by interface unit 102 equals first force level F1. With reference to FIGS. 2A to 4, in first NREM sleep stage N1 of user 10, force F applied by strap 202 on lower jaw 22 equals first force level F1.

Processor 20 is further configured to increase force F applied by interface unit 102 in a stepwise manner to a second force level F2 from first force level F1 upon detection of second NREM sleep stage N2. In other words, once user 10 transitions from first NREM sleep stage N1 to second NREM sleep stage N2 during the sleep session, processor 20 receives output signals 108 conveying information related to second NREM sleep stage N2, and force F applied by interface unit 102 is increased from first force level F1 to second force level F2. Specifically, upon detection of second NREM sleep stage N2, processor 20 controls actuating unit 104, such that force F applied by interface unit 102 equals second force level F2. With reference to FIGS. 2A to 4, in second NREM sleep stage N2 of user 10, force F applied by strap 202 on lower jaw 22 equals second force level F2.

Processor 20 is further configured to increase force F applied by interface unit 102 in a stepwise manner to a third force level F3 from second force level F2 upon detection of REM sleep stage R1. In other words, once user 10 transitions from second NREM sleep stage N2 to REM sleep stage R1 during the sleep session, processor 20 receives output signals 108 conveying information related to REM sleep stage R1, and force F applied by interface unit 102 is increased from second force level F2 to third force level F3. Specifically, upon detection of REM sleep stage R1, processor 20 controls actuating unit 104, such that force F applied by interface unit 102 equals third force level F3. With reference to FIGS. 2A to 4, in REM sleep stage R1 of user 10, force F applied by strap 202 on lower jaw 22 equals third force level F3.

From graph 400, it can be concluded that force F applied by interface unit 102 on lower jaw 22 is greater in REM sleep stage R1 and second NREM sleep stage N2 as compared to force F applied by interface unit 102 in first NREM sleep stage N1 and awake state of user 10. With reference to FIGS. 2A to 4, force F applied by strap 202 on lower jaw 22 of user 10 is greater in REM sleep stage R1 and second NREM sleep stage N2 as compared to force F applied by strap 202 in first NREM sleep stage N1 and awake state of user 10. This means that the tightness of strap 202 is progressively increased as user 10 transitions from awake state A1 to REM sleep stage R1. Therefore, during the sleep session of user 10, the degree of mouth opening of user 10 is relatively lower in REM sleep stage R1 and second NREM sleep stage N2.

In various embodiments, processor 20 is further configured to progressively increase force F applied by interface unit 102 on lower jaw 22 based on a progression of the sleep stages of user 10 from awake state A1 to REM sleep stage R1. Upon progression of the sleep stages of user 10 from awake state A1 to REM sleep stage R1, processor 20 controls actuating unit 104 to actuate interface unit 102, such that force F applied by interface unit 102 on lower jaw 22 is progressively increased from idle force level F0 to third force level F3. With reference to FIGS. 2A to 4, upon progression of the sleep stages of user 10 from awake state A1 to REM sleep stage R1, the tightness of strap 202 may also be progressively increased.

In various exemplary embodiments, during the sleep session, processor 20 controls actuating unit 104, such that mouth opening of user 10 in each of second NREM sleep stage N2 and REM sleep stage R1 is substantially the same as the mouth opening of user 10 in first NREM sleep stage N1, or awake state A1 of user 10.

Referring to FIGS. 3 and 4, to increase the tightness of strap 202, each of first lateral spring 306 and second lateral spring 308 is compressed to a desired extent, and head spring 310 is accordingly extended. A resistance of head spring 310 to extension beyond a desirable limit prevents an extra compression of first lateral spring 306 and second lateral spring 308 which may otherwise cause discomfort to user 10 due to excessive force F applied by strap 202 on lower jaw 22 (shown in FIG. 2B) of user 10. In other words, head spring 310 may prevent an excess tightness of strap 202 that may otherwise cause discomfort to user 10.

In various exemplary embodiments, processor 20 is further configured to close the mouth of user 10 upon detection of REM sleep stage R1. Once processor 20 receives output signals 108 conveying information related to REM sleep stage R1, processor 20 controls actuating unit 104 (i.e., first and second motor mechanisms 312, 314) in order to adjust (i.e., increase) force F applied by strap 202 on lower jaw 22 of user 10. Specifically, upon receiving output signals 108 conveying information related to REM sleep stage R1, processor 20 controls actuating unit 104 in order to increase the tightness of strap 202 and prevent the mouth of user 10 from opening.

In various exemplary embodiments, processor 20 is further configured to remove force F applied by interface unit 102 upon detection of awake state A1 of user 10 or an emergency medical event. With reference to FIGS. 2A to 4, once processor 20 receives output signals 108 conveying information related to awake state A1 of user 10 or an emergency medical event, processor 20 controls actuating unit 104 (i.e., first and second motor mechanisms 312, 314) in order to remove force F applied by strap 202. Removal of force F applied by strap 202 may enable user 10 to take any precautions in case of an emergency event. In an example, the emergency medical event may comprise congestion, lack of air, nasal obstruction in deep sleep stages, and so on. In an example, in case of abnormal blood oxygen levels, one or more sensors 106 (e.g., PPG sensors) may generate output signals 108 conveying the information related to abnormal blood oxygen levels and therefore, processor 20 may control actuating unit 104 to remove force F applied by interface unit 102 (i.e., strap 202) on lower jaw 22 of user 10.

In various exemplary embodiments, processor 20 is further configured to decrease force F applied by interface unit 102 upon detection of a transition from REM sleep stage R1 to another sleep stage. In an example, upon detection of a transition from REM sleep stage R1 to at least one of awake state A1, first NREM sleep stage N1, and second NREM sleep stage N2, processor 20 controls actuating unit 104 to decrease force F applied by interface unit 102 on lower jaw 22 of user 10. With reference to FIGS. 2A to 4, upon detection of a transition from REM sleep stage R1 to another sleep stage, processor 20 controls actuating unit 104 to decrease force F applied by strap 202 on lower jaw 22 of user 10.

In various exemplary embodiments, processor 20 is further configured to decrease force F applied by interface unit 102 upon detection of a bruxism event during the sleep session. In other words, upon detection of the bruxism event during the sleep session, processor 20 controls actuating unit 104 to decrease force F applied by interface unit 102 on lower jaw 22 of user 10. With reference to FIGS. 2A to 4, upon detection of the bruxism event during the sleep session, processor 20 controls actuating unit 104 to decrease force F applied by strap 202 on lower jaw 22 of user 10. A bruxism event during the sleep session is a sleep related movement disorder in which a person grinds, gnashes or clenches his/her teeth.

In various exemplary embodiments, user 10 may be a sleep apnea patient. With reference to FIGS. 2A to 4, for adjusting the degree of mouth opening of user 10, interface system 100 adjusts force F applied by interface unit 102 on lower jaw 22 of user 10 based on the current sleep stage of user 10 during the sleep session. Force F applied by interface unit 102 in the deep sleep stages (i.e., second NREM sleep stage N2 and REM sleep stage R1) is greater than force F applied by interface unit 102 in awake state A1 and the light sleep stage (i.e., first NREM sleep stage N1). In other words, each of second and third force levels F2, F3 is greater than each of idle and first force levels F0, F1. Therefore, an increased force applied by interface unit 102 in second NREM sleep stage N2 and REM sleep stage R1 may prevent the mouth of user 10 from opening during the deep sleep.

Moreover, by adjusting the degree of mouth opening of user 10 during the sleep session, the CPAP therapy may also benefit user 10 effectively. Hence, if the mouth opening of user 10 is controlled by interface system 100, there may be minimal leakage of air (provided by the CPAP therapy) out of the mouth of user 10, which may otherwise cause dryness in the sinuses, throat, and mouth. Further, due to minimal air leakage out of the mouth of user 10, user 10 may not wake up during the sleep session, which could have otherwise happened in case of air leakage in the absence of interface system 100. In this way, interface system 100 comprising interface unit 102 monitors and controls respiratory function of user 10 during the sleep session.

As the degree of mouth opening of user 10 is adjusted during the deep sleep (i.e., second NREM sleep stage N2 and REM sleep stage R1), user 10 may not feel uncomfortable in contrast to the conventional ways of preventing the mouth opening by using a medical tape or a fixed chain strap. Actuating unit 104 is configured to tighten strap 202 for preventing the mouth of user 10 from opening only when user 10 tends to open the mouth during the deep sleep. Therefore, user 10 may not feel uncomfortable while wearing interface unit 102 during the sleep session and receiving the air from the CPAP therapy. Moreover, force F (shown in FIG. 4) applied by interface unit 102 is removed upon detection of awake state A1 or the light sleep stage (i.e., first NREM sleep stage N1), or arousal of user 10. Thus, interface system 100 comprising interface unit 102 may adjust the degree of mouth opening of user 10 during the sleep session without disturbing user 10.

While interface unit 102 is preventing the mouth of user 10 from opening during the deep sleep, one or more sensors 106 continuously measure critical parameters of user 10. For example, the PPG sensors continuously measure blood oxygen saturation of user 10. In case of any emergency situation or emergency medical condition, such as abnormal blood oxygen levels, congestion, nasal obstruction, lack of air, and functional faults in the CPAP therapy, processor 20 receives corresponding output signals 108 from one or more sensors 106, and thereby controls actuating unit 104 to adjust or reduce force F applied by interface unit 102 on lower jaw 22 of user 10. In case of emergency situations, interface system 100 does not apply force F to close the mouth opening of user 10 in the deep sleep. Hence, user 10 may not experience a feeling of claustrophobia and a fear of suffocation if there is any fault in the CPAP therapy that would affect the supply of air to user 10.

Figure 5:
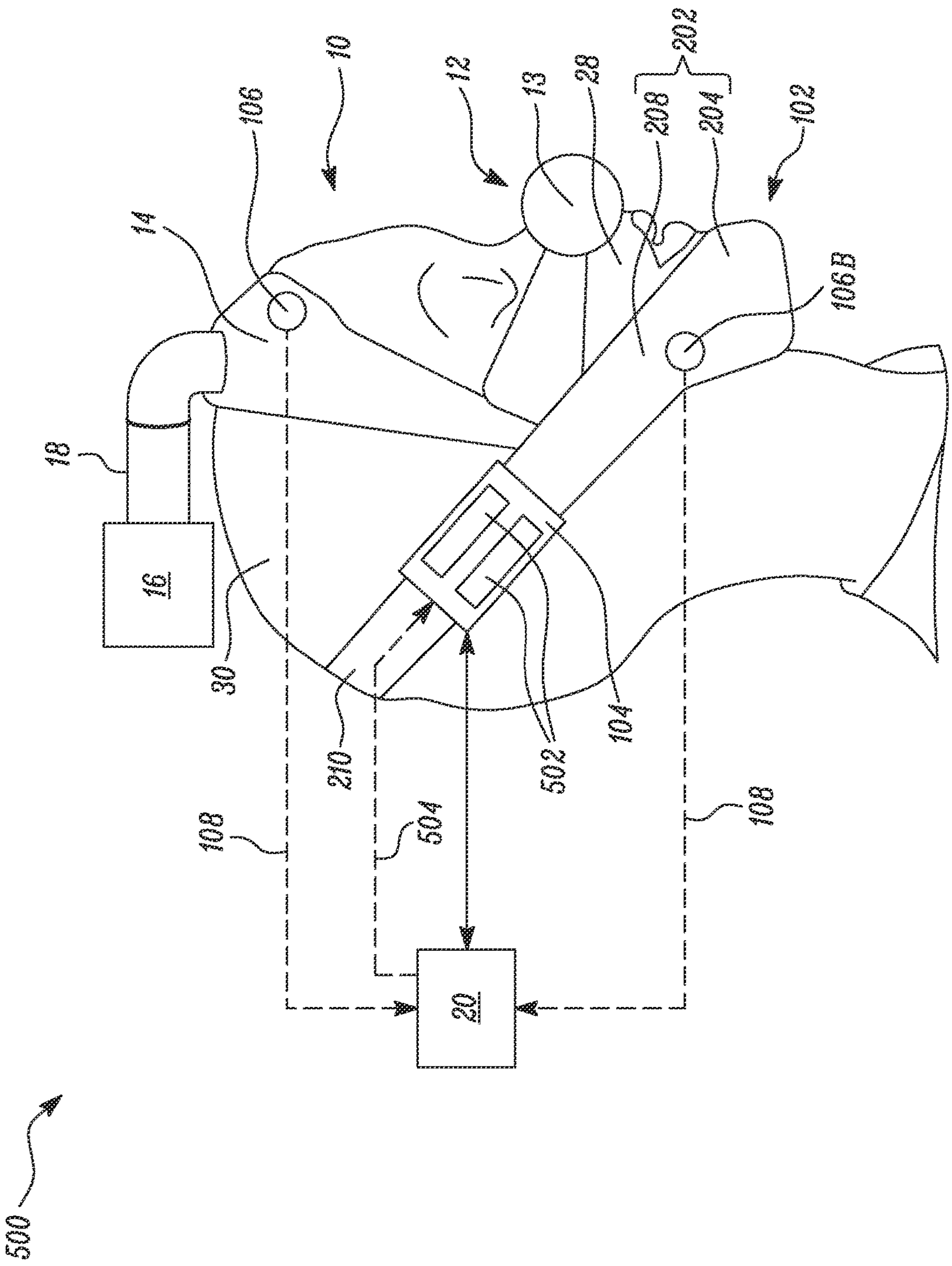
FIG. 5 is a side schematic view of the interface system of FIG. 1 for a user, according to a second embodiment of the present invention.

FIG. 5 is a schematic view of an interface system 500 for user 10, according to a second embodiment of the present invention. Interface system 500 is substantially similar to interface system 100 illustrated in FIGS. 2A to 2C, with like elements having the same numbers. However, in interface system 500, actuating unit 104 comprises one or more piezoelectric members 502 disposed on strap 202. Processor 20 is communicably coupled to one or more piezoelectric members 502 and configured to apply electric signals 504 on one or more piezoelectric members 502 to adjust the tightness of strap 202. Specifically, based on output signals 108 received from one or more sensors 106, processor 20 applies electric signals 504 on one or more piezoelectric members 502 to adjust the tightness of strap 202. Therefore, one or more piezoelectric members 502 are configured to adjust the tightness of strap 202 based on applied electric signals 504 by processor 20. In some embodiments, the tightness of strap 202 is adjusted by one or more piezoelectric members 502 in order to vary force F applied by strap 202 in various sleep stages during the sleep session according to graph 400 illustrated in FIG. 4.

Figure 6:
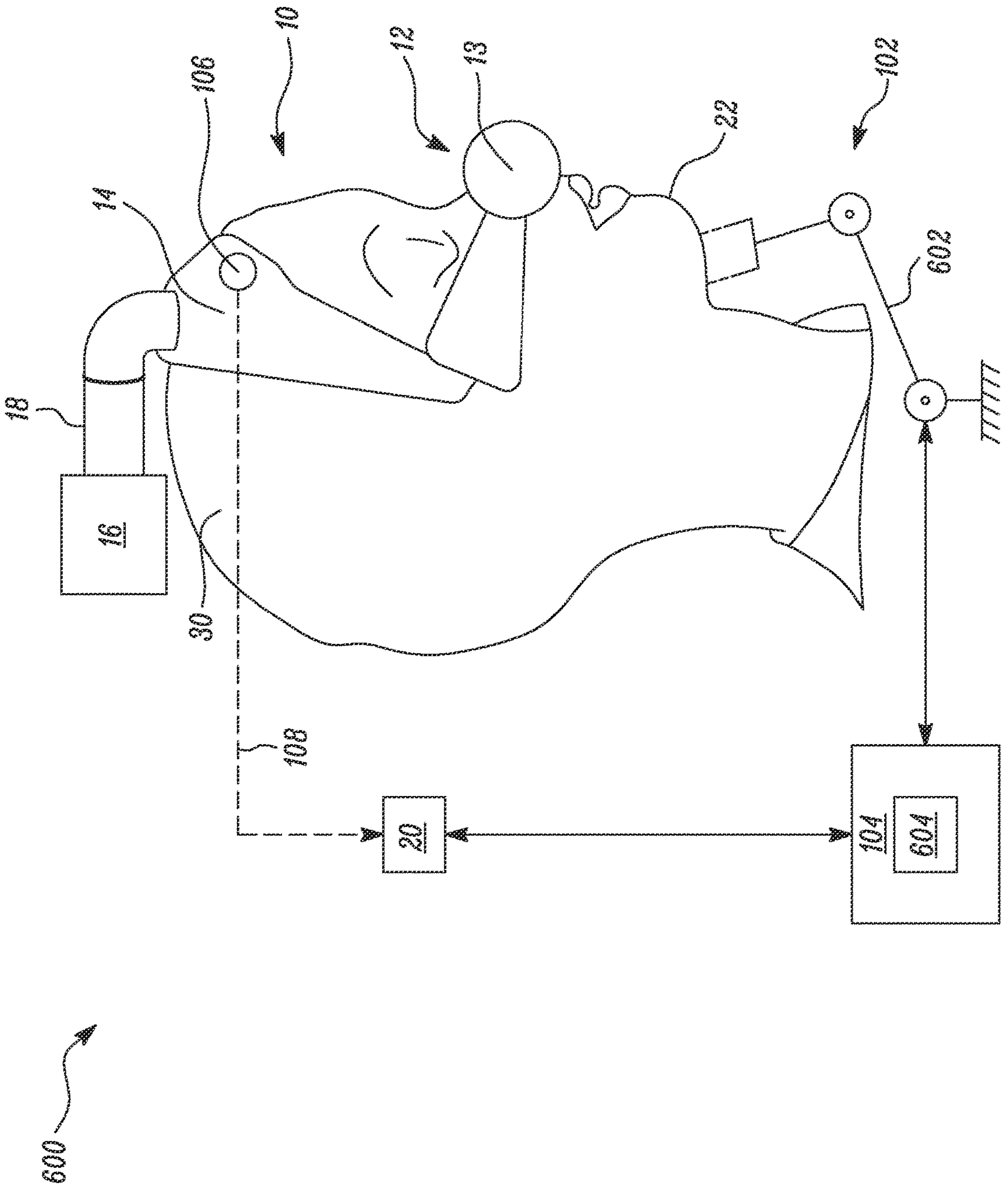
FIG. 6 is a side schematic view of the interface system of FIG. 1 for a user, according to a third embodiment of the present invention.

FIG. 6 is a schematic view of an interface system 600 for user 10, according to a third embodiment of the present invention. Interface system 600 is substantially similar to interface system 100 illustrated in FIGS. 2A to 2C, with like elements having the same numbers. However, in interface system 600, interface unit 102 comprises a robotic arm 602 (instead of a strap) configured to engage and move lower jaw 22 of user 10. Further, in interface system 600, actuating unit 104 comprises a motor mechanism 604 configured to actuate robotic arm 602. In various exemplary embodiments, motor mechanism 604 may comprise at least a rotor, a stator surrounding the rotor, an output shaft, and a winding. Components of motor mechanism 604 are not shown in FIG. 6 for illustrative purposes. The rotor is rotatable relative to the stator. The output shaft may be coupled to robotic arm 602. A rotation of the rotor of motor mechanism 604 causes turning of the output shaft which to actuate robotic arm 602.

In various exemplary embodiments, robotic arm 602 may be configured to apply force F (shown in FIG. 4) on lower jaw 22 of user 10. Upon receiving output signals 108 conveying information related to sleep stages of user 10, processor 20 controls motor mechanism 604 in order to adjust force F applied by robotic arm 602 on lower jaw 22 of user 10. By adjusting force F applied by robotic arm 602 on lower jaw 22 of user 10, the degree of mouth opening of user 10 is adjusted based on the current sleep stage of user 10 during the sleep session.

Figure 7:
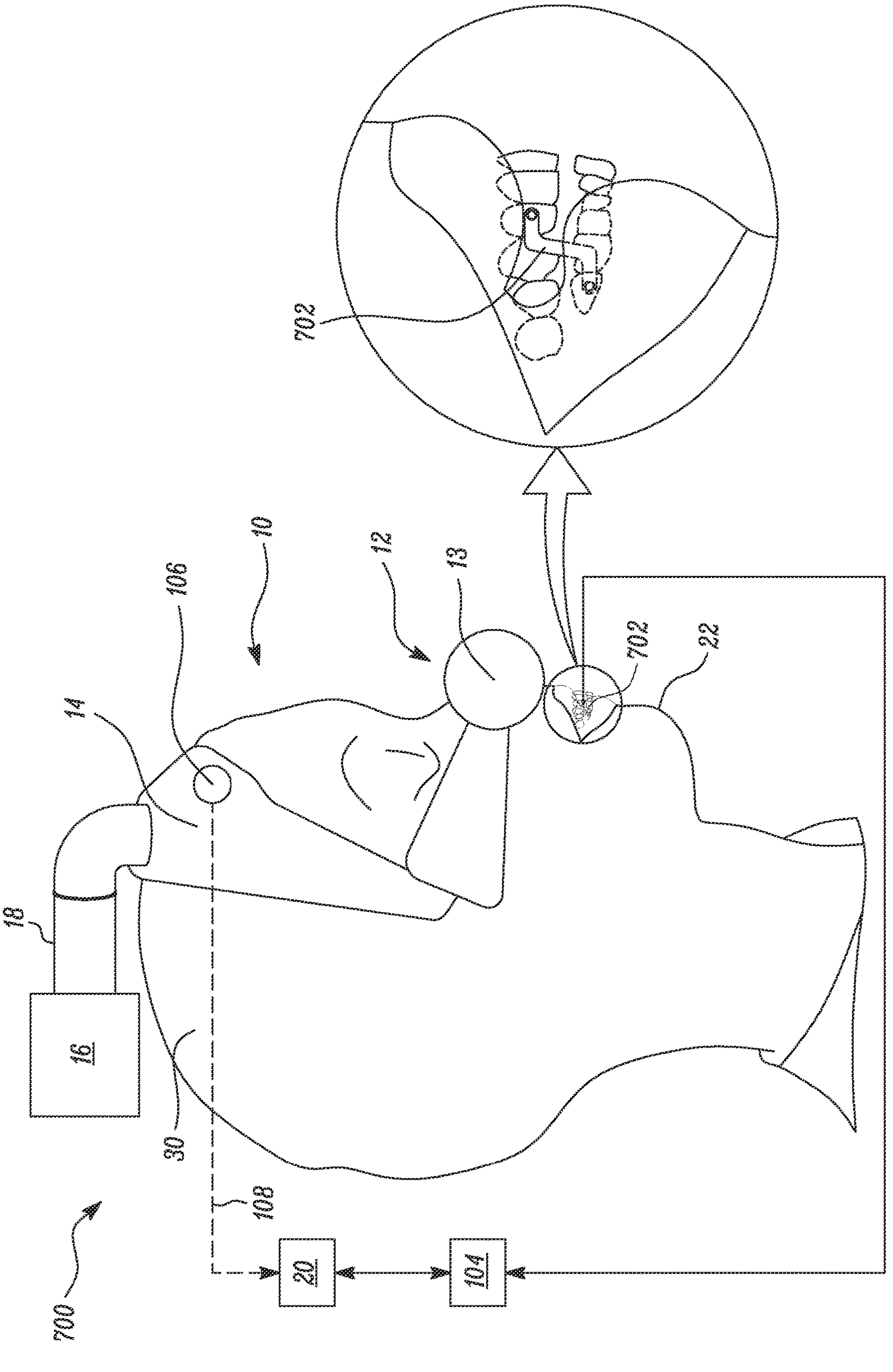
FIG. 7 is a side schematic view of the interface system of FIG. 1 for a user, according to a fourth embodiment of the present invention.

FIG. 7 is a schematic view of an interface system 700 for user 10, according to a fourth embodiment of the present invention. Interface system 700 is substantially similar to interface system 100 illustrated in FIGS. 2A to 2C, with like elements having the same numbers. However, in interface system 700, interface unit 102 comprises a mouthguard 702 (instead of strap 202) configured to be worn by user 10. A portion of the jaw is shown as transparent (indicated by dashed lines) in FIG. 7 for illustrative purposes.

Typically, a mouthguard may help in relieving obstructive sleep apnea in a person. In various exemplary embodiments, in interface system 700, actuating unit 104 may comprise motor mechanism 604 (shown in FIG. 6) configured to actuate mouthguard 702. Actuating unit 104 is configured to adjust a force applied by mouthguard 702 on lower jaw 22 of user 10. In various exemplary embodiments, mouthguard 702 may be configured to apply force F (shown in FIG. 4) on lower jaw 22 of user 10. Upon receiving output signals 108 conveying information related to sleep stages of user 10, processor 20 controls actuating unit 104 in order to adjust force F applied by mouthguard 702 on lower jaw 22 of user 10. By adjusting force F applied by mouthguard 702 on lower jaw 22 of user 10, the degree of mouth opening of user 10 is adjusted based on the current sleep stage of user 10 during the sleep session.

Figure 8:
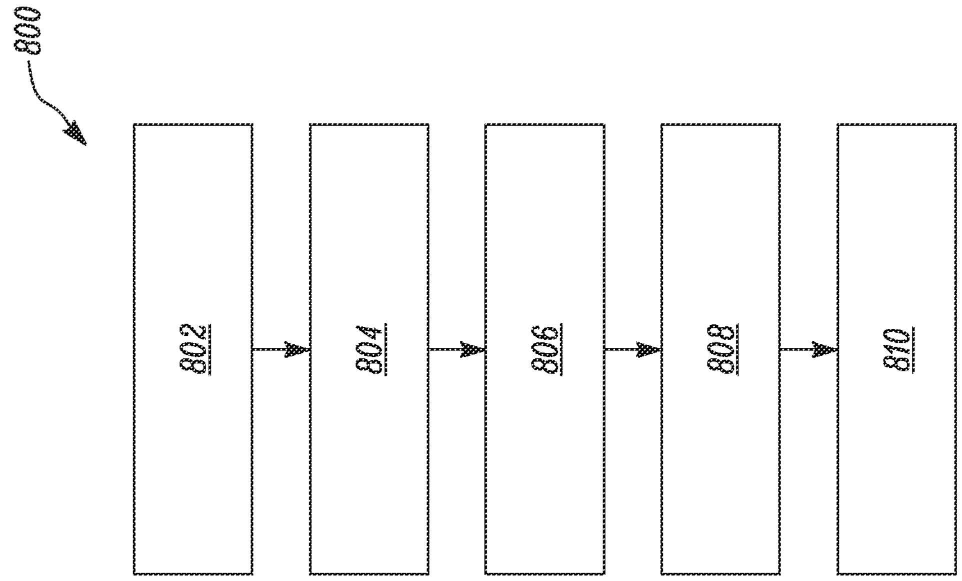
FIG. 8 is a flowchart illustrating a method for monitoring and controlling respiratory function of the user during a sleep session, according to an embodiment of the present invention.

FIG. 8 illustrates a flowchart for a method 800 for monitoring and controlling respiratory function of user 10 (shown in FIG. 2A) during the sleep session. Method 800 will be described with reference to interface system 100 and FIGS. 2A to 4. However, in other exemplary embodiments, method 800 may be applicable to interface system 500 of FIG. 5, interface system 600 of FIG. 6, and interface system 700 of FIG. 7.

At step 802, method 800 comprises engaging lower jaw 22 (shown in FIG. 2B) of user 10 with interface unit 102. Interface unit 102 is configured to selectively apply force F (shown in FIG. 4) on lower jaw 22 of user 10. At step 804, method 800 comprises providing actuating unit 104 operatively coupled to interface unit 102. Actuating unit 104 is configured to actuate interface unit 102 in order to selectively apply and adjust force F on lower jaw 22 of user 10. At step 806, method 800 comprises receiving, via processor 20, output signals 108 from one or more sensors 106 conveying information related to sleep stages of user 10 during the sleep session. At step 808, method 800 comprises determining, via processor 20, the current sleep stage of user 10 based on output signals 108 received from one or more sensors 106. At step 810, method 800 comprises controlling, via processor 20, actuating unit 104 based on the current sleep stage of user 10 to adjust force F applied by interface unit 102 on lower jaw 22 of user 10, thereby adjusting the degree of mouth opening of user 10.

There is thus provided an interface system and a method for monitoring and controlling respiratory function of a user, which overcomes the existing problems. While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

In the present invention, the expression "at least one of A, B and C" means "A, B, and/or C", and that it suffices if, for example, only B is present. A single element or other unit may fulfill the functions of several items recited in the claims. The mere fact that certain measures are recited in mutually different dependent claims does not indicate that a combination of these measures cannot be used to advantage. Any reference signs placed between parentheses in the claims should not be construed as limiting the scope of the appended claims.

What is claimed is:

1. An interface system for a user, the interface system comprising:

an interface unit configured to engage and selectively apply a force on a lower jaw of the user;

an actuating unit operatively coupled to the interface unit, wherein the actuating unit is configured to actuate the interface unit in order to selectively apply and adjust the force on the lower jaw of the user;

one or more sensors configured to generate output signals conveying information related to sleep stages of the user during a sleep session; and, a processor communicably coupled to the one or more sensors and the actuating unit, wherein the processor is configured to:

receive the output signals from the one or more sensors and determine a current sleep stage of the user during the sleep session; and, control the actuating unit based on the current sleep stage of the user to adjust the force applied by the interface unit on the lower jaw of the user, thereby adjusting a degree of mouth opening of the user.

2. The interface system of claim 1, wherein the interface unit comprises a strap configured to be at least partially worn on a chin of the user and apply the force on the lower jaw of the user based on a tightness of the strap, wherein the actuating unit is further configured to adjust the tightness of the strap on the chin of the user in order to control the degree of mouth opening, and wherein the processor is further configured to control the actuating unit to adjust the tightness of the strap based on the current sleep stage.

3. The interface system of claim 2, wherein the strap comprises a chin portion configured to be disposed on the chin of the user, a first lateral portion coupled to the chin portion and configured to be disposed on a first cheek of the user, and a second lateral portion coupled to the chin portion opposite to the first lateral portion and configured to be disposed on a second cheek of the user.

4. The interface system of claim 3, wherein the actuating unit comprises:

a first lateral spring coupled to the first lateral portion of the strap;

a second lateral spring coupled to the second lateral portion of the strap;

a first motor mechanism operatively coupled to the first lateral spring and configured to extend or compress the first lateral spring;

a second motor mechanism operatively coupled to the second lateral spring and configured to extend or compress the first lateral spring; and, a head spring configured to be disposed on a head of the user and coupled to each of the first lateral spring and the second lateral spring;

wherein an extension or a compression of each of the first lateral spring and the second lateral spring causes a corresponding compression or extension of the head spring;

wherein an extension or a compression of each of the first lateral spring and the second lateral spring causes a corresponding increase or decrease of the tightness of the strap; and, wherein the processor is communicably coupled to and configured to control the first motor mechanism and the second motor mechanism in order to adjust the tightness of the strap.

5. The interface system of claim 4, wherein the interface unit further comprises a headband configured to be worn on the head of the user and coupled to the first lateral portion and the second lateral portion of the strap, and wherein the head spring is coupled to the headband.

6. The interface system of claim 3, wherein the one or more sensors comprises a set of first sensors disposed on the first lateral portion of the strap and a set of second sensors disposed on the second lateral portion of the strap.

7. The interface system of claim 1, wherein the processor is further configured to close the mouth of the user upon detection of a rapid eye movement (REM) sleep stage.

8. The interface system of claim 7, wherein the processor is further configured to progressively increase the force on the lower jaw of the user based on a progression of the sleep stages of the user from an awake state to the REM sleep stage.

9. The interface system of claim 8, wherein the processor is further configured to remove the force on the lower jaw of the user upon detection of the awake state of the user or an emergency medical event.

10. The interface system of claim 7, wherein the processor is further configured to:

increase the force on the lower jaw of the user in a stepwise manner to a first force level from an idle force level corresponding to an awake state upon detection of a first non-rapid eye movement (NREM) sleep stage;

increase the force on the lower jaw of the user in a stepwise manner to a second force level from the first force level upon detection of a second NREM sleep stage; and, increase the force on the lower jaw of the user in a stepwise manner to a third force level from the second force level upon detection of the REM sleep stage.

11. The interface system of claim 7, wherein the processor is further configured to decrease the force on the lower jaw of the user upon detection of a transition from the REM sleep stage to another sleep stage.

12. The interface system of claim 1, wherein the processor is further configured to decrease the force on the lower jaw of the user upon detection of a bruxism event during the sleep session.

13. The interface system of claim 1, wherein the one or more sensors comprise at least one of an electroencephalogram sensor, an electrocardiogram sensor, a photoplethysmography sensor, an air flow sensor, a microphone, a humidity sensor, a carbon dioxide sensor, an accelerometer, a bioimpedance sensor, and an image sensor.

14. The interface system of claim 1, wherein at least one of the one or more sensors is configured to detect the degree of mouth opening of the user, and wherein the processor is further configured to control the actuating unit based on the degree of mouth opening of the user.

15. The interface system of claim 1, further comprising:

a respiratory interface device structured to sealingly engage an airway of the user; and, a tubing assembly disposed in fluid communication with the respiratory interface device to deliver a flow of breathing gas to the airway of the user, wherein the tubing assembly is coupled to the interface unit.

16. A method for monitoring and controlling respiratory function of a user during a sleep session, the method comprising:

engaging a lower jaw of the user with an interface unit, wherein the interface unit is configured to selectively apply a force on a lower jaw of the user;

providing an actuating unit operatively coupled to the interface unit, wherein the actuating unit is configured to actuate the interface unit in order to selectively apply and adjust the force on the lower jaw of the user;

receiving, via a processor, output signals from one or more sensors conveying information related to sleep stages of the user during the sleep session;

determining, via the processor, a current sleep stage of the user based on the output signals received from the one or more sensors; and, controlling, via the processor, the actuating unit based on the current sleep stage of the user to adjust the force on the lower jaw of the user, thereby adjusting a degree of mouth opening of the user.

17. An interface system for monitoring and controlling respiratory function of a user, the interface system comprising:

interface means for engaging and selectively applying a force on a lower jaw of the user;

actuating means for actuating the interface unit in order to selectively apply and adjust the force on the lower jaw of the user;

sensor means for generating output signals conveying information related to sleep stages of the user during a sleep session; and, processing means configured to:

determine a current sleep stage of the user based on the output signals received from the sensor means; and, control the actuating means based on the current sleep stage of the user to adjust the force on the lower jaw of the user, thereby adjusting a degree of mouth opening of the user.

* * * * *